(12) United States Patent
Malak

(10) Patent No.: US 7,328,708 B2
(45) Date of Patent: Feb. 12, 2008

(54) LED MULTIPLEX SOURCE AND METHOD OF USE OF FOR STERILIZATION, BIOACTIVATION AND THERAPY

(75) Inventor: Henryk Malak, Ellicott City, MD (US)

(73) Assignee: United Laboratories & Manufacturing, LLC, Sterling, VA (US)

( * ) Notice: Subject to any disclaimer, the term of this patent is extended or adjusted under 35 U.S.C. 154(b) by 43 days.

(21) Appl. No.: 11/135,935

(22) Filed: May 25, 2005

(65) Prior Publication Data

US 2005/0256554 A1    Nov. 17, 2005

Related U.S. Application Data

(63) Continuation-in-part of application No. 10/846,886, filed on May 17, 2004.

(60) Provisional application No. 60/670,616, filed on Apr. 13, 2005, provisional application No. 60/531,601, filed on Dec. 23, 2003.

(51) Int. Cl.
*A61B 19/00* (2006.01)

(52) U.S. Cl. .......................... 128/898; 607/88; 607/89

(58) Field of Classification Search ................ 128/898; 606/3–12, 27; 607/88–92, 96
See application file for complete search history.

(56) References Cited

U.S. PATENT DOCUMENTS 4,930,504 A * 6/1990 Diamantopoulos et al. ... 607/88
5,827,268 A * 10/1998 Laufer .......................... 606/28

* cited by examiner

*Primary Examiner*—A. Farah
(74) *Attorney, Agent, or Firm*—Nixon & Vanderhye P.C.

(57) ABSTRACT

This invention discloses an LED multiplex source and a method of using multi-band-type energies from the source for sterilization, bioactivation, and therapy of a targeted body. The LED multiplex source is a pulsed/modulated LED source with at least one different member of the group of pulsed/modulated radiation sources consisting of: an electromagnetic, acoustic, electroluminescent, thermal, and/or magnetic source. The invention also teaches how to convert heat generated by the LED multiplex source into electromagnetic radiation and uses this radiation for sterilization, bioactivation, and therapy. The LED multiplex source is an energy-efficient radiation source, is compact, and also provides sensory feedback to optimize, in real-time, sterilization, bioactivation, and therapy processes. The invented source will replace some of the existing radiation sources and, as well, will open new areas of applications.

21 Claims, 11 Drawing Sheets

LED MULTIPLEX SOURCE AND METHOD OF USE OF FOR STERILIZATION, BIOACTIVATION AND THERAPY

CROSS REFERENCE TO RELATED APPLICATIONS

This application is a continuation-in-part of U.S. patent application Ser. No. 10/846,886 filed May 17, 2004 entitled "Acusto-optical therapeutical devices and methods", U.S. provisional patent application Ser. No. 60/531,601 filed Dec. 23, 2003 entitled "Acusto-optical therapeutical devices and methods" and U.S. provisional patent application Ser. No. 60/670,616 filed Apr. 13, 2005 entitled "Use LED Technology for Sterilization and Bioactivation" each of which is incorporated by reference herein in their entirety.

STATEMENT REGARDING FEDERALLY SPONSORED RESEARCH

There is NO claim for federal support in research or development of this product.

FIELD OF THE INVENTION

This invention is related to highly efficient energy radiation sources and method of the use of them in the animal, plant and food industries and in human and animal therapy.

BACKGROUND OF THE INVENTION

There is a great need for energy efficient radiation sources which will perform multiple tasks according to the program needs. Currently in common use are radiation sources with low energy efficiency such as, incandescent lamps. The luminous efficiency of these lamps are no greater than 5% which means that 95% of the energy produced by these lamps is heat. Heat, in most applications, is not welcome. Particularly excessive heat is not needed in summertime or in countries with warmer climates. Animal farms in warmer climates are adversely affected by the lack of energy efficient electromagnetic radiation sources. Electromagnetic radiation is needed in animal farms to keep animals sterile and in sterile/odorless conditions. The excessive heat often kills animals in spite of very extensive ventilation in brooders or other facilities. Other dangers in animal farms are diseases, such as animal flu, that occurs more often in the presence of excessive heat and humidity.

In the last several years, an enormous effort has been made in the development of highly-efficient energy radiation sources, particularly related to electromagnetic radiation sources. Significant progress has been made in the development of highly efficient light emitting diodes (LEDs) whose luminous efficiency is at least twice better than incandescent lamps. LEDs are also much longer lasting light sources than incandescent lamps; therefore modern LEDs are successfully replacing lamps in traffic lights, cars, and medical devices. LEDs could also be applied in many areas of our lives, however there are still limitations in this technology. One of the limitations is the availability of LEDs of different colors. Only recently were ultraviolet LEDs demonstrated, and still there is a lack of LEDs in the far-infrared spectral range. Another continuing limitation of LED technology is their luminous efficiency. Recent advances in LED technology with organic light emitting diodes (OLEDs) show promise for brighter light sources, however there still is a question if the efforts in the development of OLEDs will be focused only on white OLEDs or will super-bright ultraviolet and infrared OLEDs also be developed. Currently, LEDs are applied successfully in dermatology for removal of acne and wrinkles, which is performed with blue and yellow LEDs respectively. Red LEDs are also used to reduce muscle pain and to increase collagen content in body. However, there are still limitations in the use of LEDs, such as using them for sterilization or as broad-band sources of illumination from UV to far-infrared. The energy efficiency of LEDs continues to require improvement in order to use them as a cost-effective choice.

SUMMARY OF THE INVENTION

This invention discloses an energy efficient LED multiplex source and a method of use of multi-band-type energies generated by the LED multiplex source for sterilization, bioactivation, and therapy. The LED multiplex source is a pulsed/modulated LED source with recovered electromagnetic radiation from heat generated by the LEDs multiplex source and with at least one different member of the group of pulsed/modulated radiation sources consisting of: electromagnetic, acoustic, electroluminescent, thermal, and/or magnetic. The selection of radiation sources being used in the LED multiplex source will depend on the application. The invention also teaches how to convert heat generated by the LED multiplex source into electromagnetic radiation and utilizes this radiation for sterilization, bioactivation, and therapy. It is proposed to use a heat-sink and outer housing made of a material capable of absorbing heat energy and emitting this energy as electromagnetic radiation. The heat-sink and outer housing are assembled with the LED multiplex source, and they absorb heat generated by the LED multiplex source and then emit this energy in the form of electromagnetic radiation. The shape of the heat-sink and outer housing promotes directional and focused electromagnetic radiation.

The invented LED multiplex source is the compact energy-efficient radiation source and additionally provides a sensory feedback to optimize in real-time sterilization, bioactivation, and therapy processes. The sensory feedback gathers information about the physical and biochemical conditions of the irradiated body and also technical parameters of the LED multiplex source. This information is administered by custom-designed software.

The invented source will replace some of the existing radiation sources and as well will open new areas of applications. For example, the LED multiplex source can be successfully applied in animal farms, where sterilization and bioactivation of animals by electromagnetic radiation and heat is very important. Currently, infrared lamps are used for these applications. However, in summertime, excessive heat produced by these lamps limit their use. The invented source is energy-efficient, will produce less heat, and most of this heat will be converted back to useful electromagnetic radiation. The LED multiplex source can also be applied in cosmetic and dermatology applications such as for acne treatment, wrinkle removal, increasing collagen content in body and other treatments. The invention also proposes a method of the use of a multi-band electromagnetic source in which the sterilization, bioactivation, and therapy are performed with wavelengths selected from UV to Near Infrared (band I), and from far-infrared radiation of 1,200 nm to 20,000 nm (band II). The light of band I will activate biochemical reactions on topical areas of the skin and far-infrared radiation of band II will penetrate deeper into the skin to sterilize bacteria, activate biochemical reactions, and deliver heat into the body.

The invention also includes the use of other radiation sources such as acoustic, electric, magnetic, thermal, and electroluminescent, to support multi-band electromagnetic sterilization, bioactivation, and therapy.

DETAILED DESCRIPTION OF PREFERRED EMBODIMENTS

1. Abbreviations and Definitions

Figure 1:
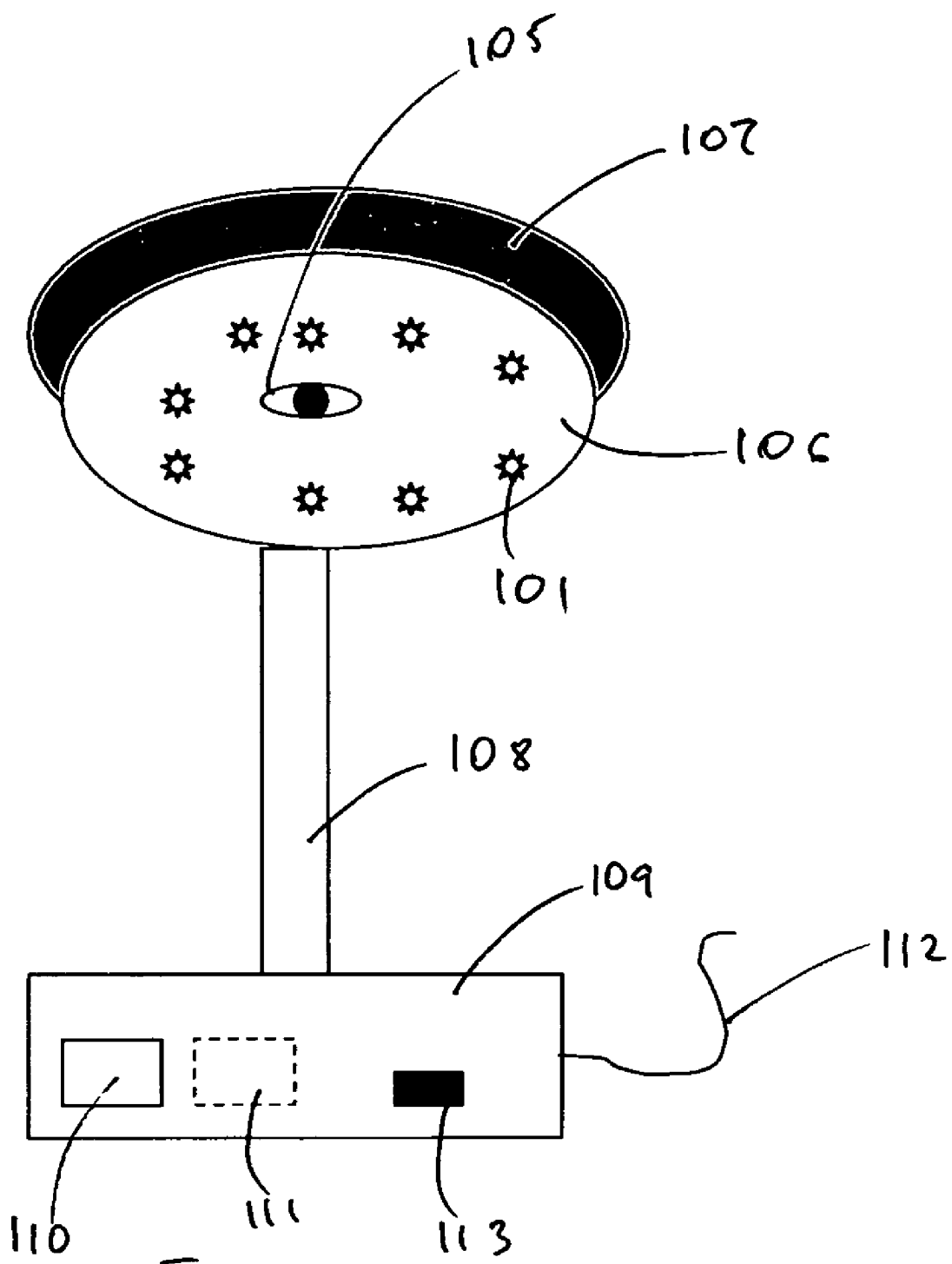
FIG. 1. A stand-alone LED multiplex source device

LED—light emitting diode
OLED—organic light emitting diode
SLD—super luminescent diode
UV light—ultraviolet light
UV-VIS-NIR light—ultraviolet, visible and near-infrared light
FIR—far infrared light
CW optical source—continuous wave optical source

2. Exemplary Embodiments

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

The invention discloses a novel LED multiplex source and a method of use of multi-band-type energies generated by the LED multiplex source for sterilization, bioactivation, and therapy. The LED multiplex source is a pulsed/modulated LED source with recovered electromagnetic radiation from heat generated by the LEDs multiplex source and with at least one different member of the group of pulsed/modulated radiation sources consisting of: electromagnetic, acoustic, electroluminescent, thermal, and/or magnetic, but not limited to them. Currently, some of these radiation sources are in use for sterilization, bioactivation and therapy. However, the specific combinations of these radiation sources used together for some applications are unique and are contemplated as a part of the invention. The using LED technology, as an efficient electromagnetic radiation source for sterilization, bioactivation, and therapy is also unique. Any advances in ultraviolet and infrared LED technology can be applied for sterilization, bioactivation, and therapy. Both of these concepts, the use of ultraviolet LED and infrared LED for sterilization, bioactivation, and therapy, are considered to be a part of this invention. Please note that the sterilization process by infrared light is different from the sterilization process by ultraviolet light. Ultraviolet light sterilizes by ionized radiation and infrared light sterilizes mainly by increasing the temperature of an irradiated body and irradiated media surrounding the body.

The LED sources in the invention includes inorganic light emitting diodes (LED), organic light emitting diodes (OLED), and super-luminescent diodes (SLD), and these sources including laser emitting diodes are preferable electromagnetic radiation sources used in this invention. The LED radiation sources are more energy-efficient, compact, can be modulated to THz frequencies and longer-lasting than traditional lamp sources. However, using both the LED and lamp sources together is also considered to be a part of this invention.

The invention uses preferably pulsed/modulated radiation sources for sterilization, bioactivation, and therapy of the body. There are sound reasons for the use of pulsed/modulated radiation sources. The pulsed/modulated radiation sources are more energy-efficient, their electronics is much smaller, they produce less heat, and most importantly, they interact more effectively with human and animal bodies, plants, and other materials. The invention considers using pulsed/modulated radiation sources with frequencies up to the terahertz range. Radiation at terahertz frequencies interacts more effectively with the irradiated body than does radiation at lower frequencies. During this interaction, radiation exchanges its energy with the irradiated body mostly in the form of heat. The invention considers using the pulsed/modulated radiation sources at a single frequency mode, multiple frequencies mode, or a composition of multiple frequencies mode. The latter frequency mode can be a composition of multiple frequencies in the form of a music piece, for example. The positive impact of music on the body bioactivation and therapy has been scientifically proven. It is important to select the frequency mode and the frequency range of the device according to the application. The selected modes can be programmed into the LED multiplex source.

Pulsed or modulated radiation sources are more effective than CW radiation sources for sterilization, bioactivation, and therapy of a targeted body, but the use of CW radiation sources is also considered as a part of the invention.

One of the embodiments of the invention relates to the utilization of recovered electromagnetic radiation from heat generated by the LED multiplex source for sterilization, bioactivation, and therapy. It is known that radiation sources are not energy-efficient and they produce heat together with radiation energy. The amount of produced heat is substantial and in most cases is not utilized and can cause problems. It is proposed to use a heat-sink and an outer housing, which are assembled with the LED multiplex source, for recovering heat energy generated by the LED multiplex source. The heat-sink and outer housing can be made of materials that absorb heat well and then very effectively emit electromagnetic radiation. Examples of such materials, but not limited to them, are: ceramic, porcelain, gypsum, and clay. The shape of heat-sinks and outer housings are designed to promote directional and focused radiation of recovered electromagnetic energy. The method of converting heat into electromagnetic radiation by the heat-sink and outer housing applies also to any device, including halogen, white light, and infrared lamps. These lamps can be designed in a way to take advantage of the heat recovery method presented here.

Figure 2:
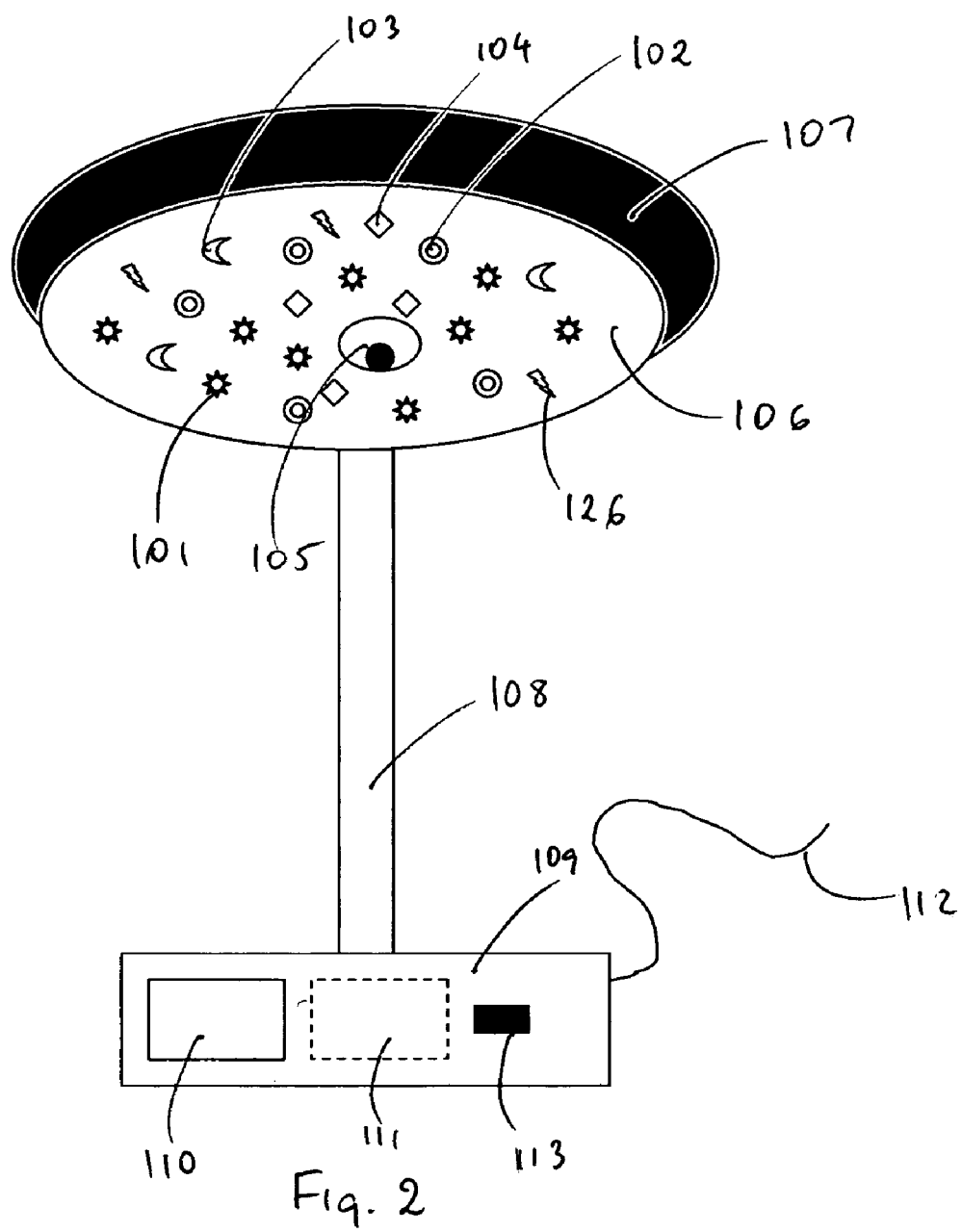
FIG. 2. A stand-alone LED multiplex source device with other energy sources
Figure 3:
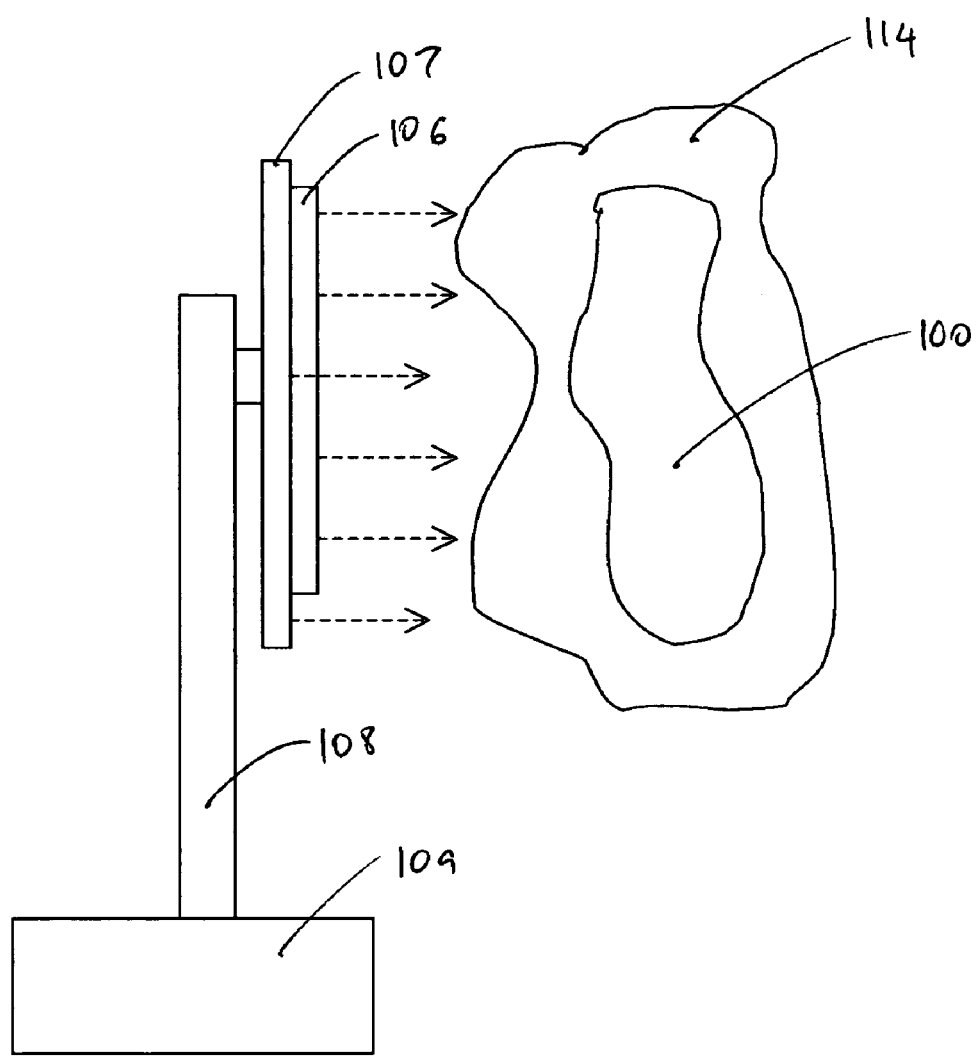
FIG. 3. A stand-alone LED multiplex source device, side view
Figure 4:
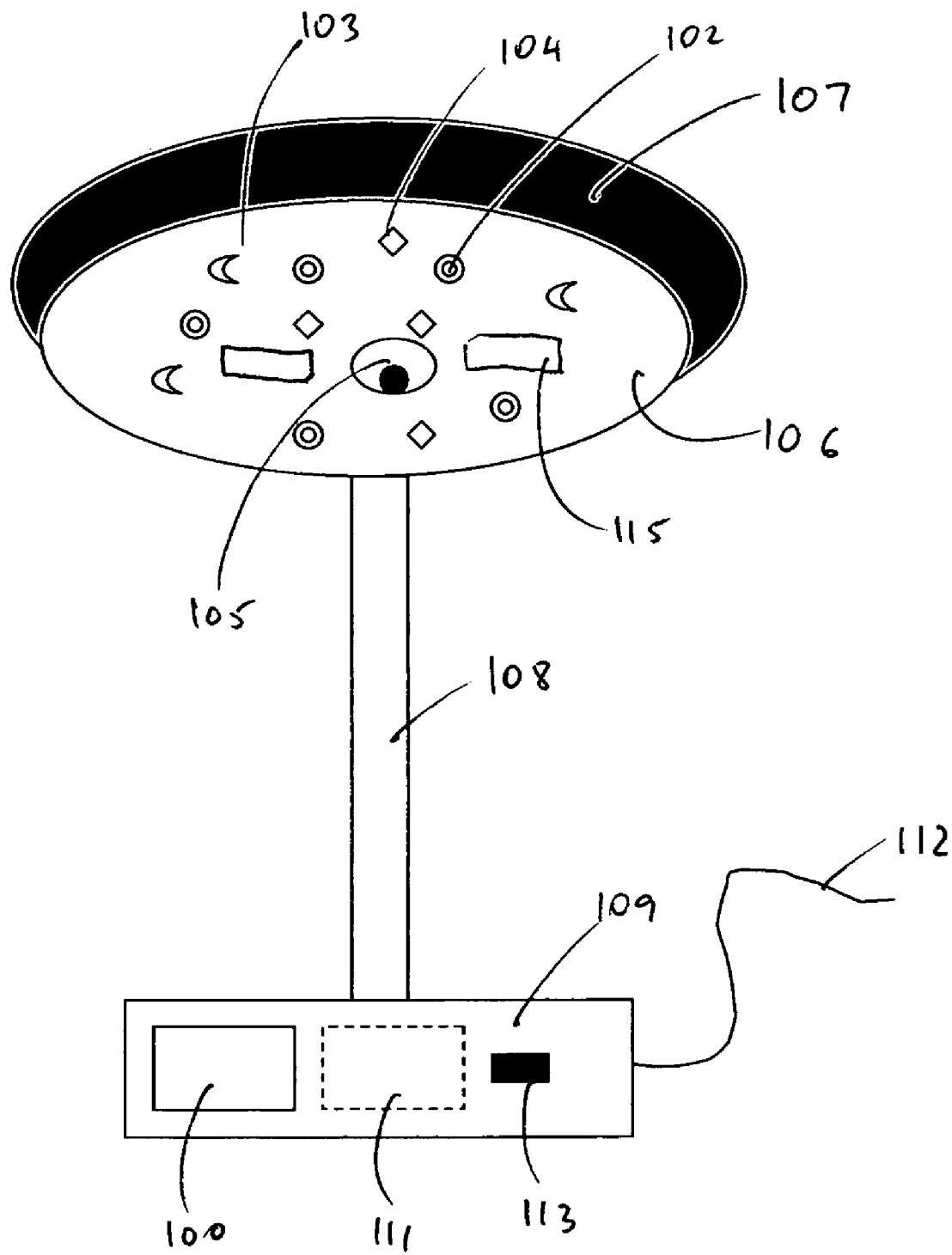
FIG. 4. A stand-alone LED multiplex source device in which the electromagnetic source is an electroluminescent source FIG. 5. A stand-alone LED multiplex source device with an incandescent lamp FIG. 6. A hand-held portable LED multiplex source device FIG. 7. An elastic-bandage LED multiplex source device FIG. 8. A heat-sink energy converter to electromagnetic radiation FIG. 9. Conversion of ultraviolet light to visible and infrared light FIG. 10. Selection of visible and infrared light from a white source of light FIG. 11. A personal sauna with a LED multiplex source FIG. 12. A hair dryer with a LED multiplex source
Figure 5:
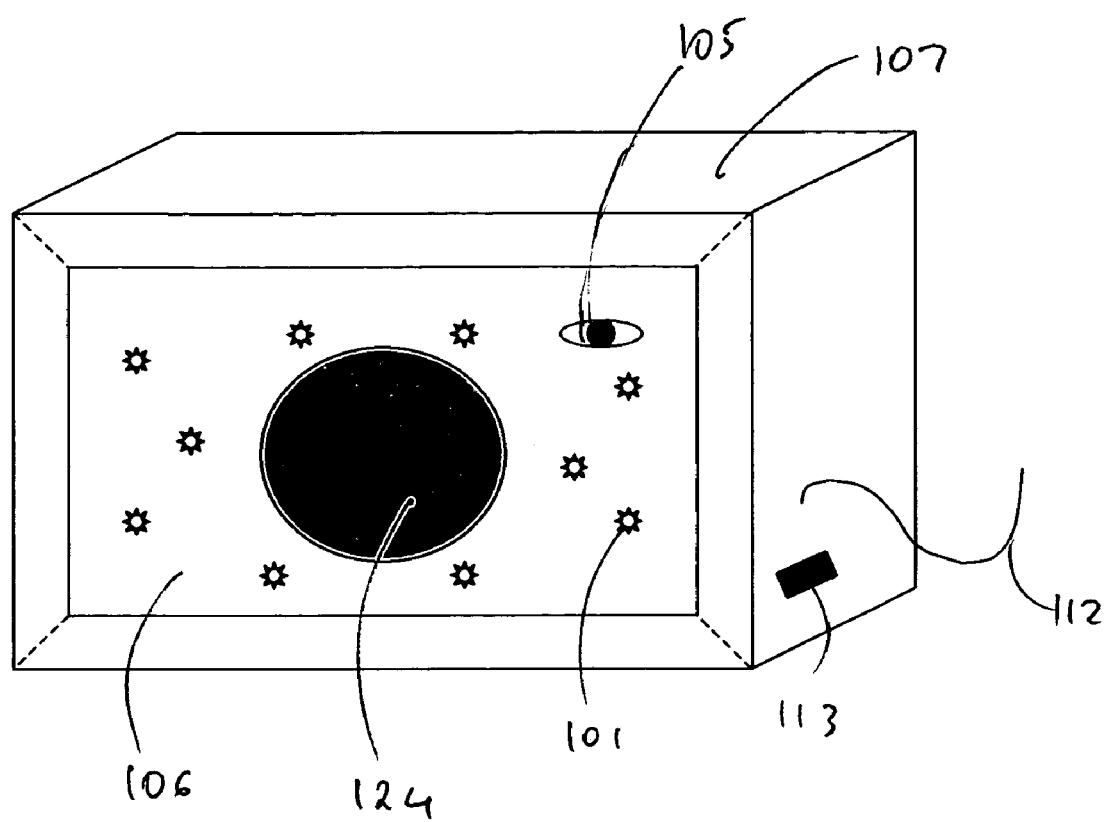
Figure 6:
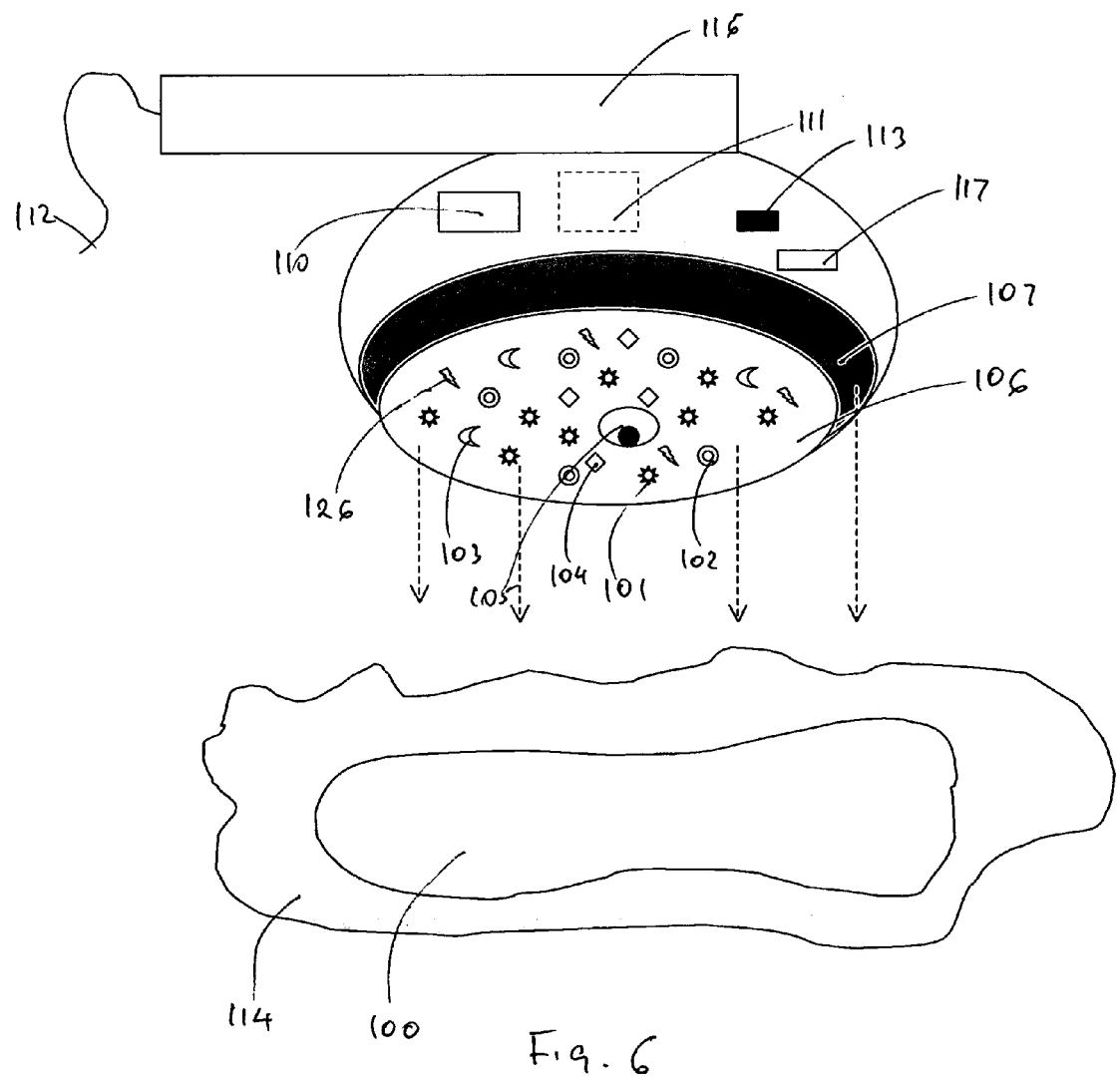
Figure 7:
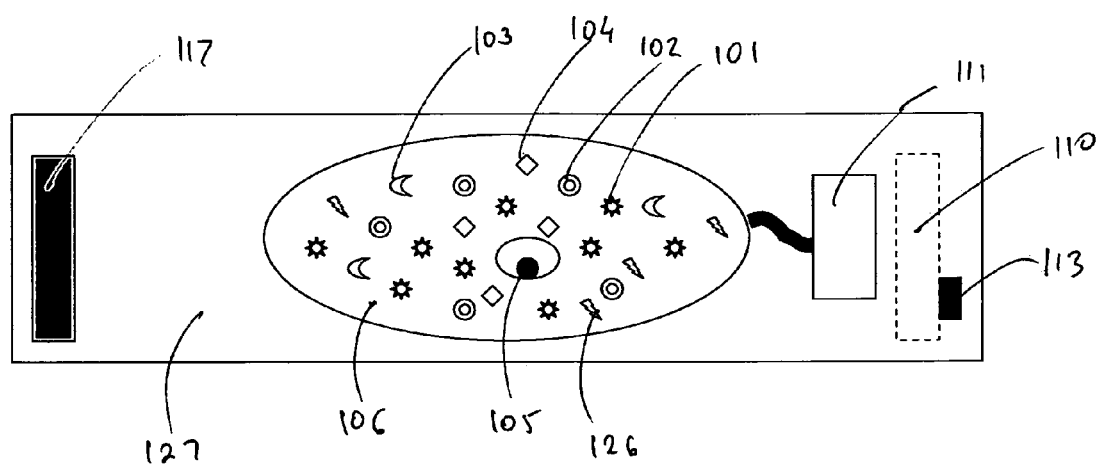

Exemplary of designs of the LED multiplex sources with the heat sinks and outer housings are shown in FIGS. 1-7. FIG. 1 shows a stand-alone LED multiplex source, which is comprised of: the LED source 101, heat-sink converter 106, sensory feedback 105, outer housing 107, stand 108, base 109, LCD display 110, computer 111, power supply 112, on/off switch 113. The LED multiplex source preferentially uses LED 101 source with plurality of LEDs, including some white LEDs, and electromagnetic radiation generated by the heat-sink converter 106. The LED multiplex source can be further provided with auxiliary radiation sources consisting of: acoustic 102, magnetic 103, thermal 126 and microwave 104 (FIG. 2). The thermal source embedded to the heat-sink converter 106 will regulate intensity of electromagnetic radiation emitted by the heat-sink converter 106. The auxiliary radiation sources can be used as needed. For example, in animal farms, electromagnetic radiation from the LEDs and the heat-sink converter can be sufficient to use in summertime, but in wintertime, additional heating from any auxiliary source may be necessary. FIG. 3 shows a side view of the LED multiplex source including a medium 114 and the targeted body 100. The LED source 101 in the LED multiplex source can be replaced with an electroluminescence source 115, as is shown in FIG. 4. An electroluminescence source is very useful as an electromagnetic source in the LED multiplex source. The light from this source is highly diffused and gently illuminates the body. Such illumination may provide some advantages in bioactivation and therapy of the body. Second, the electroluminescence source is an energy-efficient source. Third, this source can be built on a flexible material and used successfully in an elastic bandage (FIG. 7). Using the LED source with an electroluminescent source or other electromagnetic sources is a part of this invention.

The LED multiplex source can also be designed as a combination of the LED source 101 and a lamp source 124, as is shown in FIG. 5. The possibility of alternative uses of these sources can be very convenient and practical. For example, in summertime, the LED source 101 can be used and in wintertime, the lamp source 124 can be used, and during other times of the year, both sources can be used together. The use of both sources together allows use of more efficient the LED multiplex source by lowering the energy consumption of the source and taking advantage of the presence of the heat-sink converter. The auxiliary radiation sources can also be built into the LED multiplex source (not shown on FIG. 5).

The LED multiplex source can also be designed as a portable device as is shown in FIGS. 6 and 7. The power supply 112 of the LED multiplex source can be 120-240V or low voltage (12V or less), supplied from a battery 117 or a voltage converter. A hand-held LED multiplex source (FIG. 6) can be hand-held by a device handle 116 or by a strap (not-shown). The elastic bandage device shown in FIG. 7 has the same features as the LED multiplex source shown in FIGS. 1-4. The elastic bandage can be fitted onto any part of the body. The elastic bandage can also be designed in the form of a pad or blanket, which can cover larger areas of the body. The auxiliary radiation sources may not be presented in every design of the device, but they are considered as a part of this invention. The heat-sink converter 106 in the device can be, for example, a ceramic matrix 106 on which are assembled LEDs 101. Electromagnetic heat generated by the converter 106 will irradiate the body causing sterilization, bioactivation, and/or therapy. Another examples of the portable devices are a personal sauna and a hair dryer shown in FIGS. 11 and 12. In the scope of the invention are also any other portable devices, which are built and used, based on disclosed here embodiments. The thermal radiation sources 126 embedded to the portable devices play more important role than in the stand-alone devices. The portable devices can be in direct contact with the body and therefore thermal source 126 is designed to cool the body. Such thermal radiation source is designed based on Peltier effect, in which one side of the thermal radiation source is cooled and another side of the thermal radiation source is heated up. The heat generated by the thermal radiation source will be absorbed by heat-sink converter 106 and then emitted as electromagnetic radiation.

Figure 8:
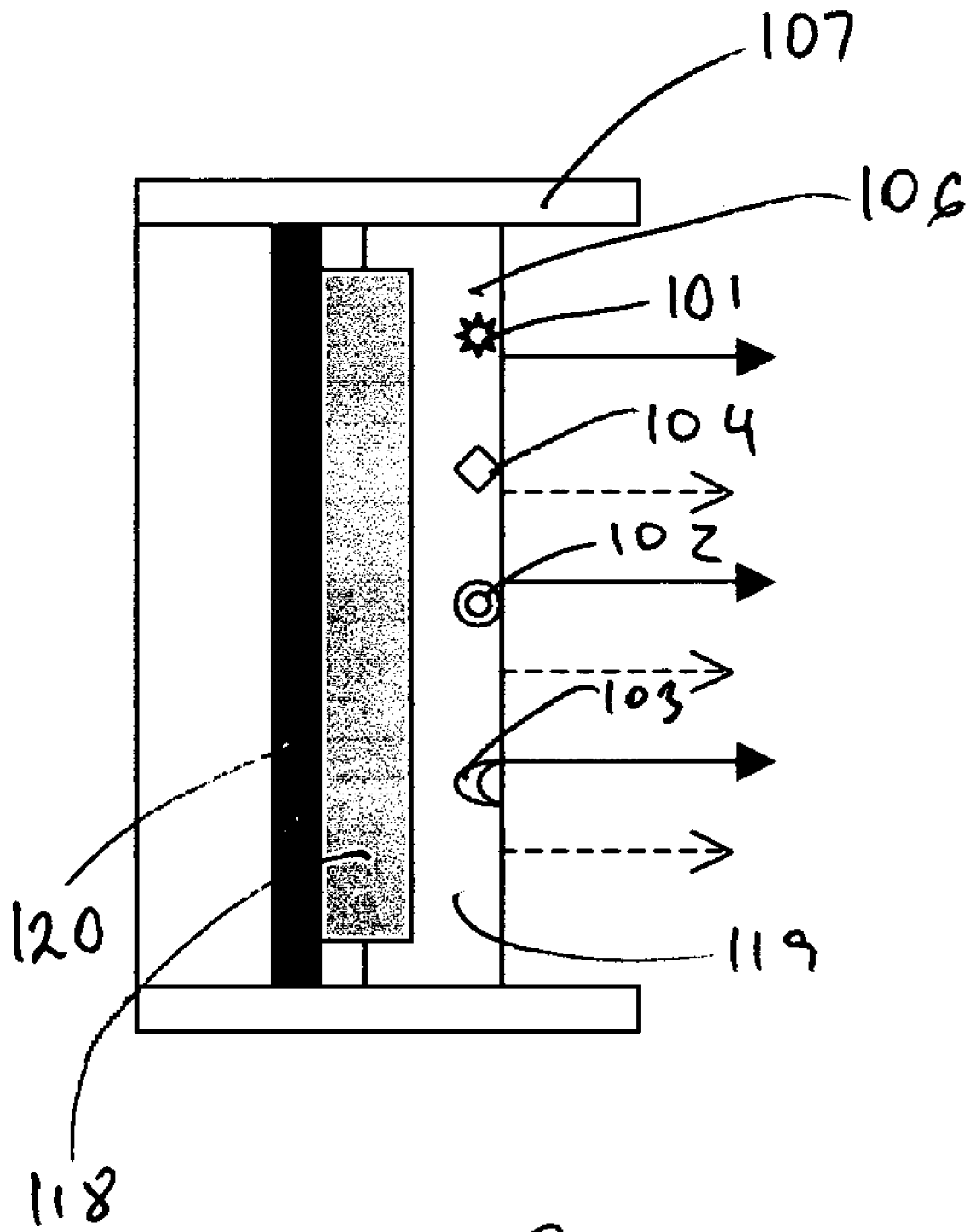

An exemplary design of a heat-sink converter is shown in FIG. 8. The radiation sources and their electronics 118 are embedded into a matrix 119. The matrix will absorb heat generated by the LED multiplex source and electronics and then the matrix 119 will emit electromagnetic radiation. Part of the heat generated by the electronics can be reflected back to the matrix 119 by a heat mirror 120. The converter can also be further provided with a heat insulator 121, which will minimize heat losses in the converter.

Heat energy recovery is also needed during the conversion of high energy electromagnetic radiation into low energy electromagnetic radiation, e.g. for an example, conversion of ultraviolet light from the LED source 101 to visible and infrared light (FIG. 8). Such conversion can be done through luminescent and non-luminescent molecules 122 which absorb higher energy photons and emit lower energy photons. Any high-energy light absorbed by a medium in which there are molecules and absorbed by an optical filter 123 are changed to heat and can be converted back into electromagnetic radiation by the heat-to-electromagnetic radiation converting properties of the optical filter 123.

Figure 9:
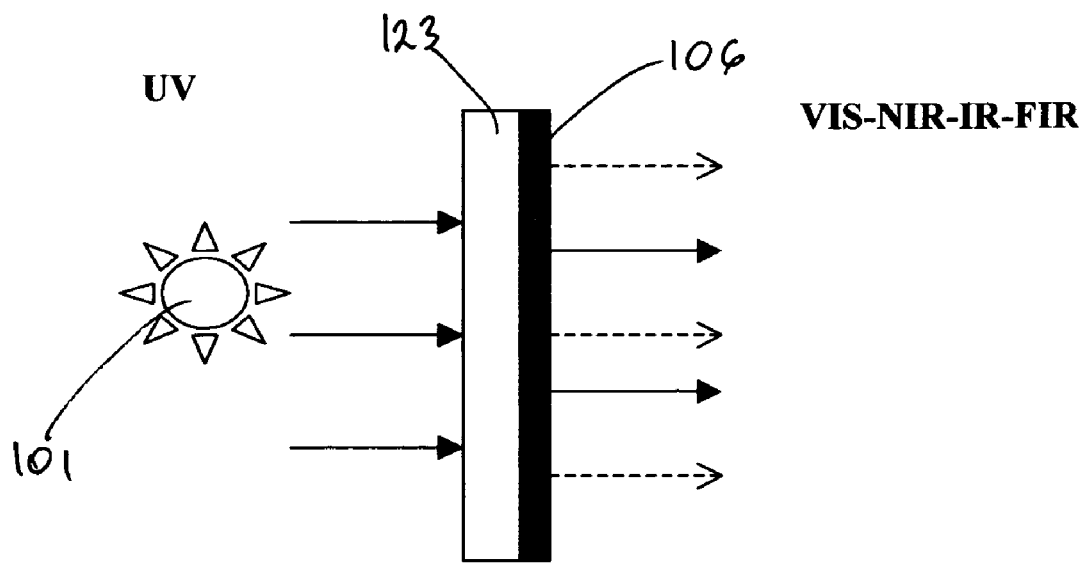
Figure 10:
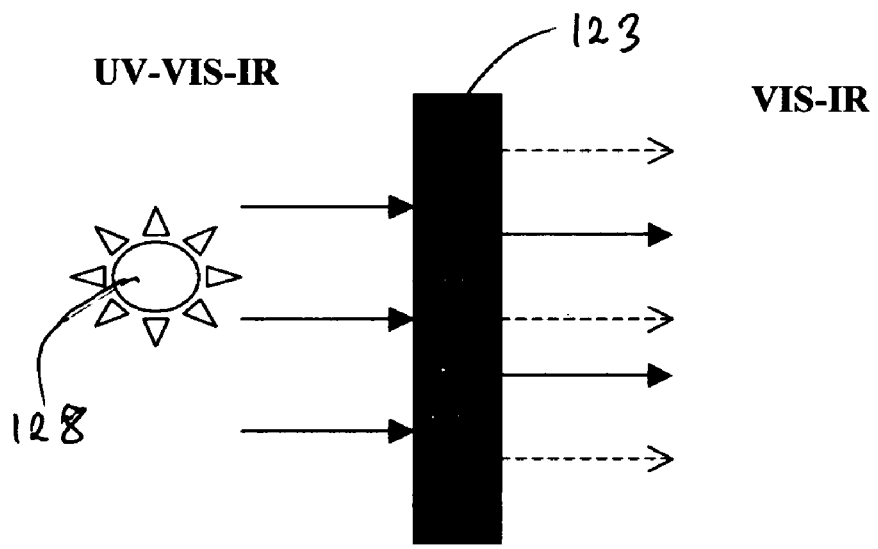

Very often, optical filters are used for selecting electromagnetic radiation at a specific spectral range from the broadband electromagnetic radiation source (FIG. 9). Most of these filters do this selection by absorbing electromagnetic radiation at wavelengths needed to be eliminated. In this process, the optical filters 123 become very hot and this heat energy can be converted into electromagnetic radiation and used for specific applications.

Another embodiment of the invention is related to the sensory feedback 105 provided in the LED multiplex source (FIGS. 1-7). The sensory feedback 105 is monitoring, in real-time, physical and biochemical parameters of the irradiated body and technical parameters of the LED multiplex source, and providing this feedback to the LED multiplex source in order to change the technical parameters of the LED multiplex source to optimize sterilization, bioactivation, therapy, or other applications. The sensory feedback is administrated by custom-designed software which is also capable to set treatment regimes based on input information from the sensory feedback and doctor's advice. The use of the sensory feedback in the LED multiplex source is crucial in many medical applications, like cosmetic treatment, wound healing, dermatological treatment, and ophthalmologic treatment, but not limited to them.

Another embodiment of the invention is related to the use of medium to enhance sterilization, bioactivation, and therapy of the body. Medium being in contact with the body may absorb some portion of radiation from the LED multiplex source. For example, water absorbs infrared radiation extremely well and wet portions of the body exposed to infrared radiation have higher temperature on the surface by several degrees compared to dry body portions. Such increased temperatures may enhance sterilization and other processes in the body.

Another embodiment of the invention uses an LED multiplex source based on LED technology for a flock brooder and other applications in animal farms. Traditionally, in these applications, infrared lamp technologies are used, where infrared lamps sterilize birds and maintain temperature in brooders. However, this technology generates excessive heat that creates problem in chicken farms in the summertime or year-round in warmer climate countries. The proposed LED technology is energy-efficient and heat generated during the production of light can be converted back into electromagnetic radiation, and used for birds' sterilization and warning, and for removing odor. The preferable spectral range of LEDs used in this application is from near-infrared to infrared, 600 nm to 20,000 nm. The LED's spectral range can be selected depending upon economical factors and technical advances in LED technology. Currently, LEDs are readily available and inexpensive in the red and near-infrared spectral range from 650 nm to 1000 nm. Light at these wavelengths penetrates human and animal bodies very well, which means that light can easily deposit its energy in the body and warm up and bioactivate the birds. Maintaining warmer bodies of chicks and young birds is very important for their growth. The LED light will also be partially absorbed by birds' feathers and cause increased feather temperature and their sterilization. Please note that most LED housings are made of plastic which is semi-transparent to far infrared radiation. The LEDs housing absorbs part of this radiation and increase its temperature few degrees. Minimizing amount of plastic in the LEDs housing will increase the contribution of far infiared radiation to the main radiation emitted by LEDs. Such a multiband LED emitter is considered to be a part of invention.

Figure 11:
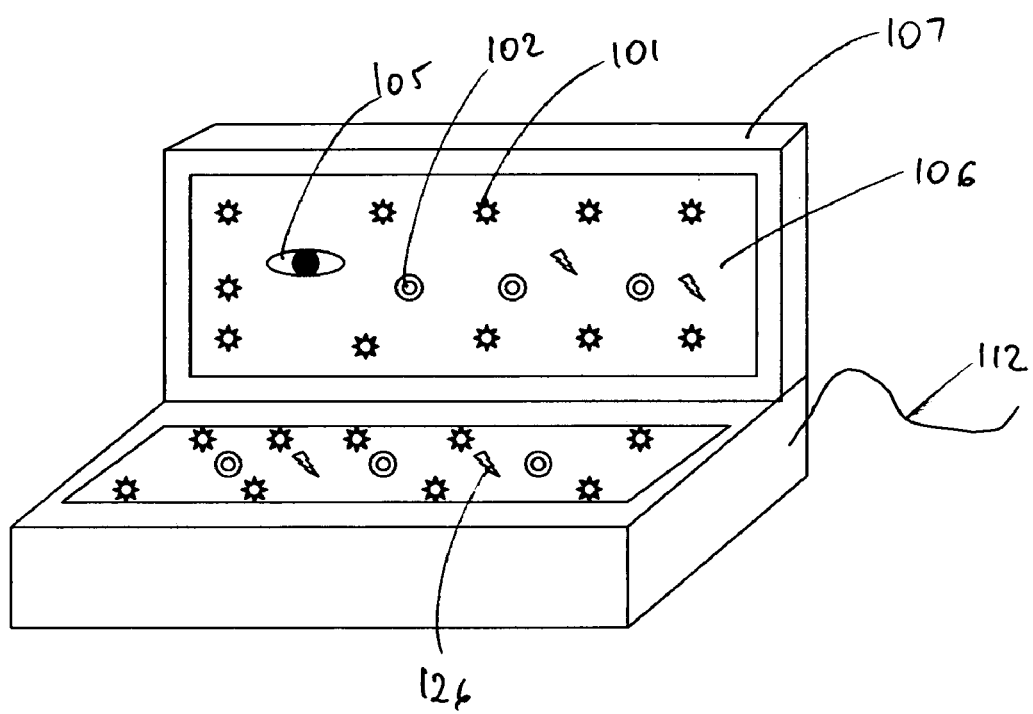

Anyone skilled in the art understands that radiation sources specific way interact with the body and deposit their energies into the body. Therefore, the selection of the radiation sources to be built into the LED multiplex source depends on applications. For example, a sauna built based on this invention will use an LED source, operating at wavelengths within a range of 600 nm to 1,200 nm, and at least two different members of the group of radiation sources consisting of: recovered electromagnetic radiation from heat having wavelengths within a range of 1,200 nm to 20,000 nm, residual heat not converted to electromagnetic radiation, thermal source 126 and acoustic source 102 (FIG. 11). Electromagnetic radiation from the LED source will penetrate, bioactivate, and treat the body, and recovered electromagnetic radiation will sterilize the surface of the body and provide heat into the body. The acoustic source, preferably a focused source, will be used in the sauna to support heat delivery to the body. The thermal source 126 will provide cooling to the body and increasing of electromagnetic radiation at far Infrared wavelengths. The invention considers using the LED multiplex source in a room sauna and in a personal sauna. There are several advantages of the sauna with an LED multiplex source versus a traditional sauna: lower operating temperatures, stronger bioactivation of the body, more effective treatment of inflammation and edema to joints, muscle, nerves, and skin, but not limited to them.

Another use of the LED multiplex source is related to cosmetic or dermatological treatment of the body. Availability of the source with two distinct bands, an ultraviolet-near infrared band I (200 nm to 1,200 nm) and far-infrared band II (1,200 nm to 20,000 nm), provide new capabilities for treatment of the body. The acne treatment by light that is a combination of blue wavelengths of the band I and far-infrared wavelengths of the band II will be very effective. Blue light will provide topical biochemical changes on skin at the depth up to 100 microns and far-infrared light will penetrate deeper into the skin up to a few millimeters and kill bacteria and induce biochemical changes within that depth.

The similar method of cosmetic/dermatological treatment can be used for wrinkle removal and/or increasing collagen build-up in the body. For these treatments, the blue LED source used for the acne treatment will be substituted with yellow and red LED sources, respectively, and the far-infrared source will remain the same. Presented treatments for acne, wrinkles, and collagen build-up are only a few examples of many applications related to this invention.

Figure 12:
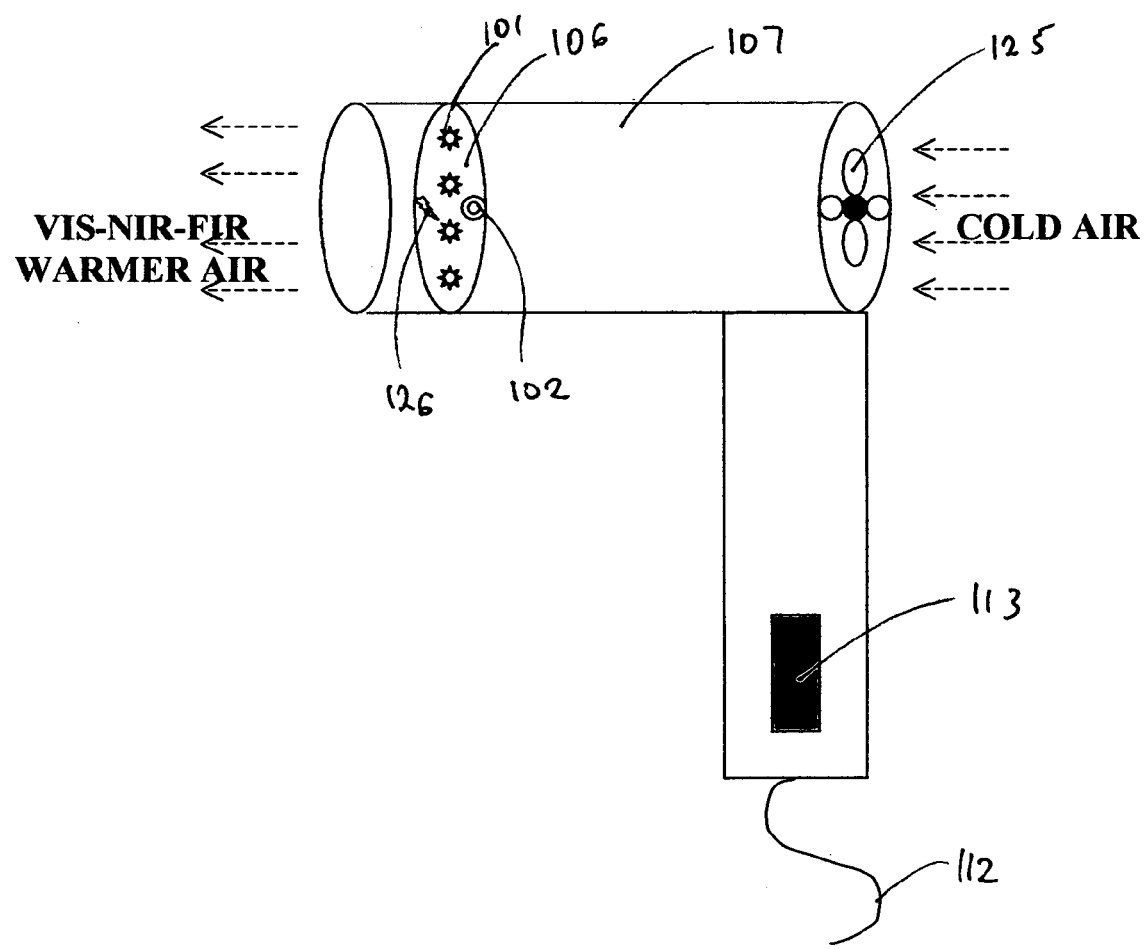

The LED multiplex source can also be applied in hair drying devices as is shown in FIG. 12. Current hair dryers do not well sterilizing hair and removing odor. They also do not rejuvenating hair and scalp. The invented hair dryer will address these uses and will bring to market new generation of hair dryers. As is shown in FIG. 12, the hart of the dryer is the LED multiplex source which is consisting of: a LED source 101 with plurality LEDs embedded to a heat-sink converter 106, acoustic focused source 102, thermal source 126. The dryer works following way. Cold air forced by a fan 125 is passing through the LED multiplex source where is slightly warm-up when thermal source 126 is off, and next the air is going out from the dryer to dry hairs. At the same time the LED multiplex source generate a VIS-NIR-IR-FIR electromagnetic radiation that irradiates hairs and drying them. Process of drying hairs by the VIS-NIR-IR-FIR electromagnetic radiation is different than by hot air. A VIS-NIR-IR part of the electromagnetic radiation is absorbed by pigments in hair causing warm-up of hairs and evaporating water from hairs. A FIR part of the electromagnetic radiation is absorbed by water covering hairs causing warm-up of water and evaporating water from hairs. The VIS-NIR-IR part of the electromagnetic radiation can be designed to have spectrum band for a specific color of hair that will provide effective bioactivation/therapy of hairs and scalp during drying hair. The dryer can also be used strictly for bioactivation/therapy hairs and scalp without the need of drying hairs. The thermal source 126 and acoustic focused source in the hair dyer can be use as needed as auxiliary radiation sources. The hair dryer is just the example how the invention can be applied.

What is claimed is:

1. A method for using multi-band-type energies from a multiplex source for sterilization, bioactivation, and therapy comprising the steps of:

surrounding a targeted body with a medium for enhancing sterilization, bioactivation and therapy of said targeted body, irradiating said targeted body and said medium with a multiplex source of multi-band-type energies for purposes of sterilization, bioactivation, and therapy of said targeted body, wherein said multiplex source is a LED source and/or a laser diode source and at least one different member selected from the group consisting of radiation sources consisting of: an electromagnetic source, an acoustic source, an electroluminescent source, a thermal source, an electrical source, and a magnetic source, and using a heat-sink energy converter to convert heat generated by said multiplex source into electromagnetic radiation which is utilized for sterilization, bioactivation, and therapy.

2. The method of claim 1, wherein said targeted body is a human body, animal body, cells, tissue, skin, joint, nerves, body fluid, plant, food, microbe, fungi, medical supply, laboratory supply, beverage, household material, solid state material, gas, or liquid.

3. The method of claim 1, wherein said medium is air, gas, water vapor, water, ice, liquid, solid state material ointment, liquid with a dissolved radiation absorbing substance, gas with a dissolved radiation absorbing substance, ointment with a dissolved radiation absorbing substance, or solid state material with a doped radiation absorbing substance.

4. The method of claim 1, wherein said electromagnetic radiation source is at least one member selected from the group consisting of: a laser, a laser diode, a lamp, a LED, a microwave source, an electroluminescent source, a fluorescence source, a phosphorescence source, and a chemiluminescence source.

5. The method of claim 4, wherein said electromagnetic radiation source comprises: said LED source with plurality LEDs.

6. The method of claim 4, wherein said electromagnetic radiation source comprises: said LED source with a plurality of LEDs and said lamp.

7. The method of claim 4, wherein said electromagnetic radiation source comprises: said LED with plurality of LEDs, and said microwave source.

8. The method of claim 1, wherein said electromagnetic radiation source is generating radiation as a single spectral band or multiple spectral bands within a spectral range of ultraviolet to microwaves.

9. The method of claim 1, wherein members of said multiplex source are pulsing/modulating at frequencies within a range of 1 Hz to 100 THz.

10. The method of claim 1, wherein members of said multiplex source are pulsing/modulating in a single frequency mode or multiple frequencies mode.

11. The method of claim 1, wherein members of said multiplex source are CW sources.

12. The method of claim 1, wherein said heat-sink energy converter and or an outer housing are made of a material capable of absorbing heat and converting absorbed heat to electromagnetic radiation.

13. The method of claim 1, wherein an optical filter is used to convert electromagnetic radiation of higher photon energy generated by said LED multiplex source to electromagnetic radiation of lower photon energies for the purpose of using converted electromagnetic radiation of lower photon energies for sterilization, bioactivation, and therapy.

14. The method of claim 13, wherein said optical filter is selected from the group consisting of an optical polarizer, optical diffuser, band-pass optical filter, long-pass optical filter, short-pass optical filter, luminescent film, and optical component with heat-to-electromagnetic radiation converting property.

15. The method of claim 1, wherein said targeted body has, on a body surface and/or inside said targeted body, a natural pigment or an artificial pigment which enhances absorption of radiation from said multiplex source for purposes of sterilization, bioactivation, and therapy.

16. The method of claim 1, wherein said LED multiplex source is a portable device, stand-alone device.

17. The method of claim 16, wherein said portable device is a hand-held massager, elastic-bandage device, pad device, clothing, personal sauna, hair dryer, toothbrush, or hairbrush.

18. The method of claim 1, wherein said multi-band-type energies are electromagnetic radiation of different photon energies from ultraviolet to microwaves and at least one different member of the group of radiation energy consisting of: acoustic, electroluminescent, thermal, electric, and magnetic.

19. The method of claim 1 wherein said multi-band-type energies is applied to poultry industry, animal industry, food industry, plant industry, beverages industry, pharmaceutical industry, biological and medical research, medicine, cosmetic treatment, dermatology, dentistry, sterilization materials, sterilization air, drug delivery, removing odor, residential housing, commercial housing, laboratory, public place, car, spa room, sauna room, spa bed, green house, plane, or household appliance.

20. The method of claim 1, further comprising the step of monitoring a sensory feedback for the purposes of optimizing sterilization, bioactivation, and therapy of said targeted body.

21. The method of claim 1, wherein the LED multiplex source comprises: said multiplex source assembled with said heat-sink energy converter, an optical filter, and a power supply.

* * * * *